United States Patent [19]

Asato

[11] 3,994,924

[45] Nov. 30, 1976

[54] 4,5,6,7-TETRA HYDRO-7-OXOBENZO(B)THIEN-4-YL ISOCYANATE AND ISOTHIOCYANATE

[75] Inventor: Goro Asato, Titusville, N.J.

[73] Assignee: American Cyanamid Company, Stamford, Conn.

[22] Filed: Nov. 4, 1975

[21] Appl. No.: 628,714

[52] U.S. Cl. .................... 260/332.3 P; 260/329 S; 424/275; 71/90
[51] Int. Cl.² .................................... C07D 333/16
[58] Field of Search .................. 260/329 S, 332.3 P

[56] References Cited
UNITED STATES PATENTS 3,944,567  3/1976  Asato .......................... 260/332.3

Primary Examiner—James O. Thomas, Jr.
Assistant Examiner—A. Siegel
Attorney, Agent, or Firm—Denis A. Polyn

[57] ABSTRACT

The present invention relates to 4,5,6,7-tetrahydro-7-oxobenzo[b]thien-4-yl isocyanate and isothiocyanate, which are novel and useful intermediates for the preparation of 4,5,6,7-tetrahydro-7-oxobenzo[b]thien-4-ylurea and thiourea compounds which are animal growth promoters.

The present invention also relates to methods of preparation for the above-identified thienyl isocyanates and isothiocyanates.

5 Claims, No Drawings

4,5,6,7-TETRAHYDRO-7-OXOBENZO(B)THIEN-4-YL ISOCYANATE AND ISOTHIOCYANATE

BACKGROUND OF THE INVENTION

The compounds of the present invention are useful and valuable intermediates for the preparation of 4,5,6,7-tetra-hydro-7-oxobenzo[b]thien-4-ylurea and thiourea compounds which possess animal growth regulating and herbicidal activity; said thienylurea and thiourea compounds having been described and claimed in the Application for United States Letters Patent Ser. No. 436,827 filed Jan. 25, 1974 now abandoned, and its continuation-in-part Ser. No. 532,449 filed Dec. 13, 1974 (Goro Asato, inventor), both of which are herein incorporated by reference.

SUMMARY OF THE INVENTION

This invention relates to compounds of the formula

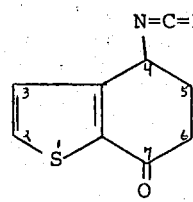

(I)

wherein X is oxygen or sulfur and said compounds are the racemic mixture, or the optical isomers thereof.

This invention also relates to methods of preparation of the above-identified formula (I) compounds.

In accordance with this invention the formula (Ia) compound wherein X is oxygen, i.e. 4,5,6,7-tetrahydro-7oxobenzo[b]thien-4-yl isocyanate can be prepared from 4,5,6,7-tetrahydro-7-oxobenzo[b]thiophen-4-amine of formula (II), or its acid addition salt by reacting the same with phosgene in the presence of an anhydrous organic solvent such as benzene, toluene, xylene, chlorobenzene or chlorinated hydrocarbons, and if preferred, under a blanket of inert gas such as nitrogen. The reaction with the amine is initially carried out at a temperature between about 0° and 40° C, preferably 10° to 20° C, and then heated to between about 50° and 100° C, and preferably 60° to 80° C, while the reaction of the amine salt is carried out between 50° and 150° C, and preferably 100° to 120° C, as graphically illustrated below:

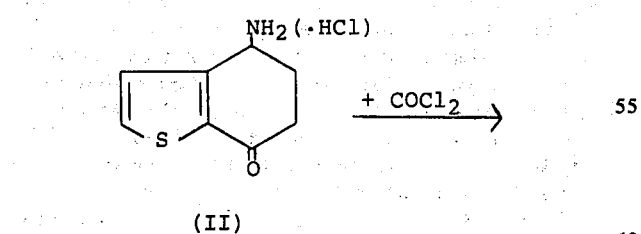

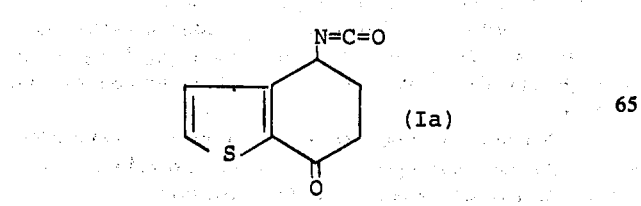

Alternatively, formula (Ia) isocyanate can be prepared by reacting the N-formyl-4,5,6,7-tetrahydro-7-oxobenzo-[b]thiophen-4-amine of formula (IIIa) with phosgene in the presence of a tertiary amine, e.g. triethylamine, in an inert solvent such methylene chloride and other chlorinated hydrocarbons at a temperature between about 0° and 50° C and preferably between 15° and 30° C to obtain 4,5,6,7-tetrahydro-7-oxoben-zo[b]thien-4-yl isocyanide of formula (IV), which is then oxidized with dimethylsulfoxide (DMSO) in the presence of anhydrous p-toluenesulfonic acid (pTSA) at a temperature between about 25° and 75° C, and preferably 25° and 50° C. The above-described reaction sequence may be graphically illustrated as follows:

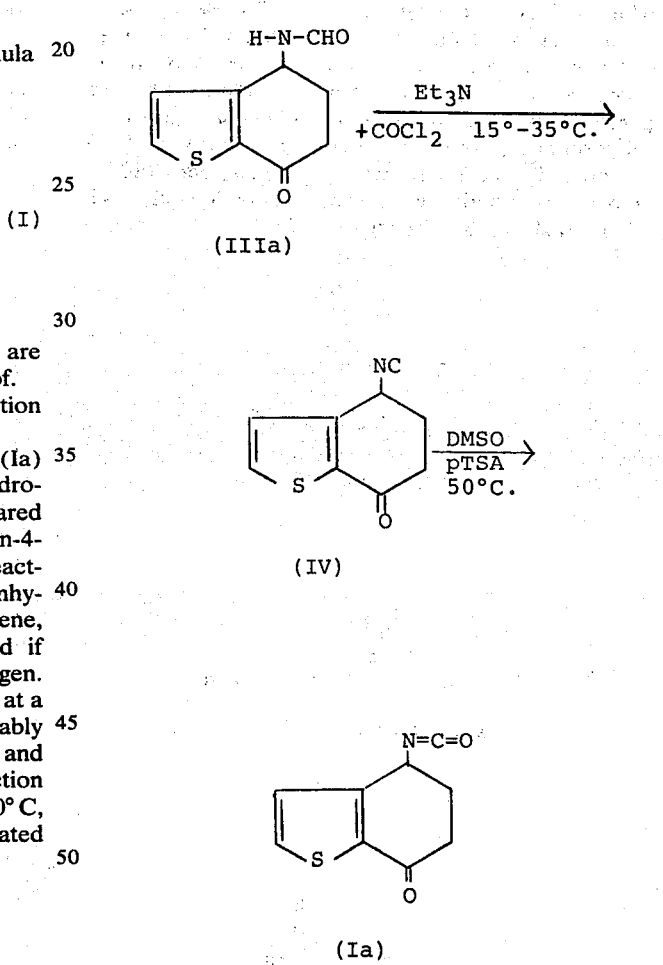

The formula (Ib) compound wherein X is sulfur, i.e. 4,5,6,7-tetrahydro-7-oxobenzo[b]thien-4-yl isothiocyanate can be prepared by reacting 4,5,6,7-tetrahydro-7-oxobenzo[b]thiophen-4-amine of formula (II) with equimolar amounts of carbon disulfide, triethylamine and a carbodiimide represented by the formula: G—N=C=N—G wherein G is cyclohexyl, cycloheptyl, alkyl $C_4$-$C_8$, and the like. This reaction is generally conducted in the presence of a solvent such as tetrahydrofuran, ethyl acetate, or an ether such as diethyl ether, at a temperature between about −10° and +80° C, and preferably between −10° and +50° C. The above reaction may be graphically illustrated as follows:

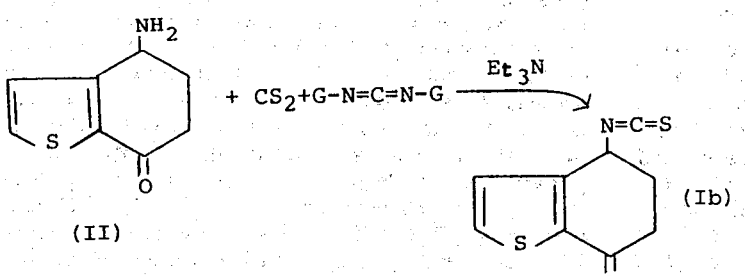

wherein G is cyclohexyl, cycloheptyl or alkyl $C_4$–$C_6$.

The intermediate 4,5,6,7-tetrahydro-7-oxobenzo-[b]thiophen-4-amine of formula (II), common to the above-described processes, may be conveniently prepared by the following reaction sequence: 4,5,6,7-tetrahydrobenzo[b]-thiophen-4-amine of formula (V) is formylated or acylated with a $C_2$–$C_4$ acid anhydride or chloride to obtain the corresponding formula (VI) amide as shown hereinbelow:

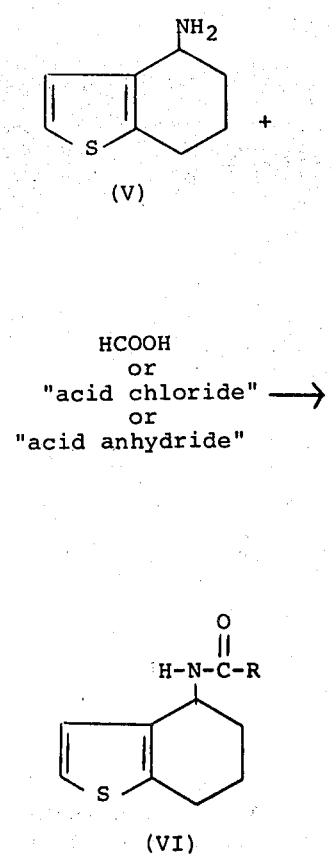

wherein R is hydrogen or $C_1$–$C_3$. The resulting formula (VI) amide is then reacted with a 2 to 8 mole equivalent, preferably with a 2 to 5 mole equivalent, of an oxidizing agent selected from the group consisting of ceric ammonium nitrate, ceric sulfate, chromic anhydride, sodium or potassium bichromate, at a temperature between about 0° and 100° C, preferably 20° C and 60° C, in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid or chromic anhydride-acetic anhydride followed by hydrolysis. The above reaction scheme may be graphically illustrated as follows:

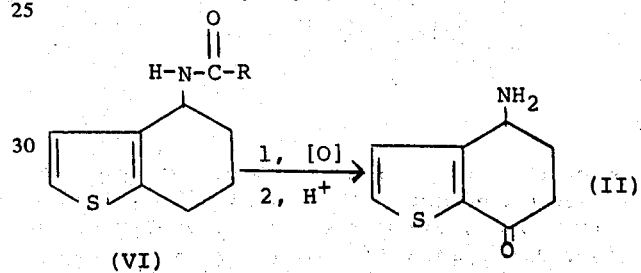

wherein R is hydrogen or alkyl $C_1$–$C_3$.

All of the hereinbefore described preparations of 4,5,6,7-tetrahydro-7-oxobenzo[b]thien-4yl isocyanate and isothiocyanate yield racemic (dl) mixtures. Should the optically active isomers of said compounds be desired, the racemic mixture of 4,5,6,7-tetrahydrobenzo[b]thiophen-4-amine (V) is initially treated with (R)-(+)-N-benzoylglutamic acid to afford a salt with the (+)-4,5,6,7-tetrahydrobenzo[b]thiophen-4-amine. It is not necessary to employ more than one mole of the resolving acid for each 2 moles of the racemic amine, as a cheaper acid, preferably acetic acid, can be substituted for the balance of the required acid. The resolved salt, (+)-4,5,6,7-tetrahydrobenzo[b]thiophen-4-ammonium (R)-N-benzoyl glutamate salt is then treated with alkali to liberate the (+)-amine, which is then isolated by standard and converted to the (−)-N-acetyl derivative of structure (VI) by treatment with acetic anhydride. Correspondingly, the remaining (−) amine is resolved with (S)-(−)-N-benzoylglutamic acid and converted to the (+) acetamide of structure (VI). The above-mentioned reactions are then carried out to obtain the optically active keto isocyanates.

As stated before, the compounds of this invention as defined by formula (I) above, are useful and valuable intermediates for the preparation of 4,5,6,7-tetrahydro-7-oxobenzo[b]thien-4-ylurea and thiourea compounds, which possess animal growth regulating properties and are the subject of the above-named applications.

The above-named ureas and thioureas can be prepared by reacting a formula (I) compound of the present invention with an amine of formula

in approximately equimolar amounts in presence of a solvent selected from the group consisting of water, $C_1$–$C_3$ alcohols, tetrahydrofuran, dioxane, ethylene glycol dimethyl ether, diethylene glycol dimethyl ether, acetone, methyl ethyl ketone and the like, and mixtures thereof. The above reaction may be graphically illustrated as follows:

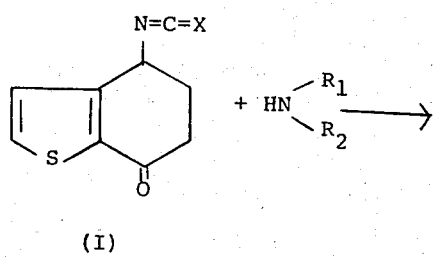

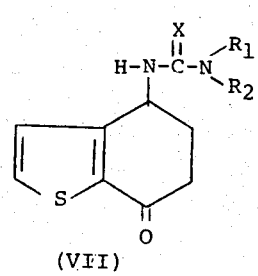

wherein X is oxygen or sulfur; $R_1$ is hydrogen or alkyl $C_1$–$C_4$; $R_2$ is hydrogen, alkyl $C_1$–$C_{12}$, hydroxy, alkoxy $C_1$–$C_4$, allyl, 2-propynyl, phenoxy, 2-methylene furan, and when $R_1$ and $R_2$ are taken together, they represent a cyclic system selected from cyclopropyl and cyclobutyl; and when $R_1$ and $R_2$ are taken together with the nitrogen to which they are attached, they represent morpholino, piperidino and pyrrolidino. Although the reaction may be conducted at superatmospheric pressure and temperatures as high as 100° C, it is generally preferable to conduct the reaction at atmospheric pressure at a temperature between 0° and 80 ° C.

As hereinbefore mentioned, the 4,5,6,7-tetrahydro-7-oxobenzo[b]thien-4-ylurea and thiourea compounds of formula (VII) are useful as growth promoting agents for farm animals.

In practice, a growth-promoting amount of a formula (VII) tetrahydro oxobenzo[b]thienylurea or thiourea, or an optically active isomer thereof, is administrated to a host animal usually in, or with, the animals feed. When administered in the feed, usually about 0.0001 to 0.08% by weight, preferably 0.001 to 0.04% by weight, of the formula (VII) urea (or thiourea), is effective for increasing growth rate.

However, said compound may also be administered as one or more subcutaneous implant(s) under the skin of said animal or as a parenteral injection. When administered to said animals as a subcutaneous implant or parenteral injection, usually in amounts that will supply about 0.001 mg to 0.2 mg, preferably 0.001 mg to 0.10 mg, per kg of body weight per day of the active compound, will produce the desired improvement in weight gain.

The present invention is further illustrated by the non-limiting examples set forth below.

SPECIFIC DISCLOSURE

EXAMPLE 1

Preparation of 4,5,6,7-Tetrahydro-7oxobenzo[b]thien-4-yl isothiocyanate

A solution of 4,5,6,7-tetrahydro-7-oxobenzo[b]thiophen-4-amine (1.68 g) in ethyl acetate (25 ml) is stirred under a nitrogen atmosphere and triethylamine (1.37 ml) added. The solution is cooled in an ice-bath for 15 minutes and carbon disulfide (0.66 ml) added. A white solid forms. After stirring for 15 minutes at 5° to 10° C, a solution of dicyclohexylcarbodiimide (2.1 g) in ethyl acetate (25 ml) is added dropwise. The reaction mixture is then stirred overnight at room temperature and filtered. Evaporation of the filtrate to dryness in vacuo affords the crude title isothiocyanate, with an infrared absorbance at 2075 cm$^{-1}$.

EXAMPLE 2

Preparation of 4,5,6,7-Tetrahydro-7-oxobenzo[b]thien-4-yl isocyanate and urea

Conversion of 4,5,6,7-tetrahydro-7-oxobenzo[b]thiophen-4-amine hydrochloride to 4,5,6,7-tetrahydro-7-oxobenzo[b]thien-4-yl isocyanate is accomplished by heating a toluene mixture of the amine hydrochloride at reflux while phosgene is introduced. After the mixture becomes less cloudy, it is cooled and filtered. Evaporation of the filtrate affords the crude 4,5,6,7-tetrahydro-7-oxobenzo[b]thien-4-yl isocyanate with an infrared absorbance at 2250 cm$^{-1}$.

Addition of ammonia/methanol solution to this isocyate affords 4,5,6,7-tetrahydro-7-oxobenzo[b]thien-4-ylurea.

EXAMPLE 3

Preparation of 4,5,6,7-Tetrahydro-7-oxobenzo[b]thien-4yl isocyanide

A sample of N-formyl-4,5,6,7-tetrahydro-7-oxobenzo[b]thiophen-4-amine (5.0 g) is dissolved methylene chloride (250 ml) under a nitrogen atmosphere and triethylamine (5.95 g) is added. Phosgene is then bubbled into the solution at 15° C and an exothermic reaction occurs. The temperature of the reaction mixture rises from 20° to 35° C and after 45 minutes, drops to 30° C. The flow of phosgene is terminated and nitrogen is then bubbled into the solution for about 20 minutes followed by ammonia gas. A brown precipitate is formed during the ammonia addition. The flow of ammonia gas is stopped when the reaction mixture becomes alkaline. The mixture is then flushed with nitrogen and is filtered to remove the precipitate. The filtrate is evaporated to dryness in vacuo, the residue is dissolved in ethanol (50 ml), the solution is filtered and evaporated to dryness in vacuo. The residue is scratched to afford a light brown solid, which is washed with water, dried and recrystallized from hexane-acetone to afford 2.1 g of the title isocyanide, m.p. 74° to 77° C.

EXAMPLE 4

Preparation of 4,5,6,7-Tetrahydro-7-oxobenzo[b]thien-4-yl isocyanate

A solution of 4,5,6,7-tetrahydro-7-oxobenzo[b]thien-4-ylisocyanide (9.5 g) in dry dimethylsulfoxide (4.63 g) is stirred under a nitrogen atmosphere while anhydrous p-toluenesulfonic acid (0.93 g) is added in small portions over an hour. The mixture is heated below 50° C. After 1.25 hours the reaction mixture is cooled and ether (3 × 3 ml) added, and the ether solution is then decanted. The ether solution contains the title isocyanate, and is used as is.

EXAMPLE 5

Preparation of 1-Methoxy-3-(4,5,6,7-tetrahydro-7-oxobenzo[b]thien-4-yl)urea

The crude ether solution of 4,5,6,7-tetrahydro-7-oxobenzo[b]thien-4-yl isocyanate prepared in Example 4 is added dropwise to a mixture of methoxyamine hydrochloride (9.02 g), triethylamine (13.67 g) and ether (50 ml) under a nitrogen atmosphere. After stirring for 36 hours at room temperature, the solid in the reaction mixture is collected and washed with water. The water-insoluble solid is recrystallized twice from acetone-hexane to afford the title urea, m.p. 185° to 188.5° C.

EXAMPLE 6

Preparation of 4,5,6,7-Tetrahydro-7-oxobenzo[b]thien-4-isocyanate

A mixture of 4,5,6,7-tetrahydro-7-oxobenzo[b]thiophen-4-amine hydrochloride (0.5 g), diisopropyl ethylamine (0.31 g) and benzene (20 ml) is cooled in an ice bath to 0° C and 7.1 ml of 12.5% solution of phosgene in benzene is added. The mixture is stirred at 10° to 15° C for 10 minutes and then at room temperature for 0.5 hour to afford a solution of the title isocyanate. The isocyanate has an infra red absorption band at 2225–2250 cm$^{-1}$. The mixture is filtered and the filtrate may be used as is for the preparation of ureas.

EXAMPLE 7

Preparation of N-Formyl-4,5,6,7-Tetrahydro-7-oxobenzo[b]thiophen-4-amine

A solution of N-formyl-4,5,6,7tetrahydrobenzo[b]thiophen-4-amine (60 g) in 50% aqueous acetic acid (1,112 ml) is stirred and ceric ammonium nitrate (727 g) is added over 20–25 minutes at 25° to 30° C. The mixture is stirred at room temperature for 15 minutes, saturated with sodium chloride and extracted with methylene chloride (2 × 770 and 1 × 400 ml). The combined methylene chloride extracts are washed with brine (380 ml) and then with water (155 ml). The water wash is extracted with methylene chloride (155 ml) and this extract is combined with the main methylene chloride extract. The methylene chloride is evaporated and the residue is triturated with ether (250 ml), collected and washed with ether to afford the title formamide, m.p. 104° to 110° C.

EXAMPLE 8

Preparation of 4,5,6,7-Tetrahydro-7-oxobenzo[b]thiophen-4-amine hydrochloride A mixture of N-formyl-4,5,6,7-tetrahydro-7-oxobenzo[b]thiophen-4amine (45.3 g), 95% ethanol (450 ml) and dilute hydrochloric acid (90 ml concentrated HCl diluted with water to 450 ml) is heated at reflux for 2.5 hours with stirring. The mixture is evaporated to dryness and the residue further dried by adding ethanol and removing the solvent in vacuo. This procedure affords 47.3 g of dark brown solid which is then stirred with 10% aqueous sodium hydroxide (473 ml) under a nitrogen atmosphere. The alkaline mixture is extracted with chloroform (3 × 473 ml), the combined extracts dried with anhydrous sodium sulfate and then decolorized with activated carbon. The mixture is filtered through diatomaceous earth and the filtrate evaporated to dryness to afford the brown colored title amine. The amine is converted to the hydrochloride salt by adding concentrated hydrochloric acid (20 ml) in 95% ethanol (250 ml). Removal of the ethanol affords 41.4 g of 4,5,6,7-tetrahydro-7-oxobenzo[b]thiophen-4-amine hydrochloride, m.p. 225° to 227° C, dec.

EXAMPLE 9

Preparation of 1-Methyl-3-(4,5,6,7-tetrahydro-7-oxobenzo[b]thien-4-yl)thiourea A mixture of 4,5,6,7-tetrahydro-7-oxobenzo[b]thien-4-ylisothiocyanate (5.0 g) and methylene chloride (100 ml) is stirred and a saturated solution of methylamine in ethanol (15 ml ethanol saturated with methylamine) added. The mixture is stirred for 15 hours then heated at reflux for 2 hours, cooled and evaporated to dryness in vacuo. The residue is triturated with water, the title thiourea collected and dried.

Similarly, substitution of isopropylamine and dimethylamine for methylamine affords 1-isopropyl- and 1,1-dimethyl-3-(4,5,6,7-tetrahydrobenzo[b]thien-4-yl)thiourea, respectively.

EXAMPLE 10

Mouse Growth Regulant Tests

CFI female mice from Carworth Farm are received when they are 6 weeks old. They are housed 10 to a cage in air-conditioned rooms (72° to 76° F) with automatically controlled lights, 14 hours on and 10 hours off. The basal diet used in these studies in Purina Laboratory Chow (see description below), which is supplied ad libitum. Water is also allowed ad libitum.

Thirteen days after arrival, the mice are weighed in groups of 10 and assigned at random to the different treatments. The concentration of the different compounds in the diet is indicated in the following Tables. Twelve days later the mice are weighed again and the experiment terminated. At least 3 cages (30 mice) of untreated controls are included in each test. Test data are provided in Table I below wherein data are reported as percent weight gain over controls. The following is a description of the diet to which the growth promoting compounds are added.

Diet

| GUARANTEED ANALYSIS | |
|---|---|
| Crude protein not less than | 23.0% |
| Crude fat not less than | 4.5% |
| Crude fiber not more than | 6.0% |
| Ash not more than | 9.0% |

INGREDIENTS

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

Table I

Effectiveness of 4,5,6,7-Tetrahydro-7-oxobenzo[b]thien-4-ylureas as Animal Growth Promoting Agents Reported as Percent Weight Gain Over Controls Using Mice as the Test Animal

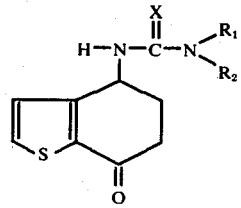

| Rate ppm in Diet | X | $R_1$ | $R_2$ | % Weight Gain Over Controls |
|---|---|---|---|---|
| 400 | O | H | H | 134 |
| 200 | O | CH$_3$O— | H | 71 |
| 400 | S | CH$_3$ | H | 62.6 |

I claim:
1. A compound of the formula:

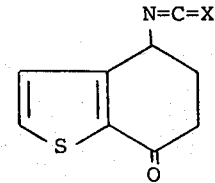

wherein X is oxygen or sulfur, the racemic mixture or the optical isomers thereof.

2. The racemic mixture according to claim 1, wherein X is oxygen; 4,5,6,7-tetrahydro-7-oxobenzo[b]thien-4-yl isocyanate.

3. The optical isomers according to claim 1, wherein X is oxygen; 4,5,6,7-tetrahydro-7-oxobenzo[b]thien-4-yl isocyanate.

4. The racemic mixture according to claim 1, wherein X is sulfur; 4,5,6,7-tetrahydro-7-oxobenzo[b]thien-4-yl isothiocyanate.

5. The optical isomers according to claim 1, wherein X is sulfur; 4,5,6,7-tetrahydro-7-oxobenzo[b]thien-4-yl isothiocyanate.

* * * * *